US00PP10965P

United States Patent [19]

Wagner

[11] Patent Number: Plant 10,965

[45] Date of Patent: Jun. 22, 1999

[54] BEGONIA PLANT NAMED 'SOLENIA LIGHT PINK'

[75] Inventor: Konrad Wagner, Hann. Münden, Germany

[73] Assignee: Gebr. Man C.V., Aalsmeer, Netherlands

[21] Appl. No.: 08/938,578

[22] Filed: Sep. 26, 1997

[51] Int. Cl.[6] ..... A01H 5/00

[52] U.S. Cl. ..... Plt./348

[58] Field of Search ..... Plt./87.18

*Primary Examiner*—Elizabeth Kemmerer

*Attorney, Agent, or Firm*—C. A. Whealy

[57] ABSTRACT

A distinct cultivar of Begonia plant named 'Solenia Light Pink', characterized by its numerous large and attractive medium pink fully double flowers that are about 7 cm in diameter; uniform and compact plant habit; dark foliage color; resistance to Powdery Mildew under commercial greenhouse conditions; and outstanding weather-tolerance and garden performance.

1 Drawing Sheet

The present invention relates to a new and distinct cultivar of Begonia plant, botanically known as a Begonia Elatior Hybrid, commercially known as Elatior Begonia, and referred to by the cultivar name Solenia Light Pink.

The new cultivar was discovered by the inventor in a controlled environment in Amstelveen, The Netherlands, as a naturally-occurring mutation of the Begonia Elatior Hybrid cultivar Solenia Rosa (disclosed in U.S. Plant patent application Ser. No. 08/854,291). The new cultivar was observed as a single plant in a group of plants of the parent cultivar. The selection of this plant was based on its lighter pink flower color compared to the flower color of plants of the parent cultivar. Plants of the new Begonia are similar to plants of the parent cultivar in all other characteristics.

Asexual reproduction of the new cultivar by top cuttings taken in a controlled environment in Amstelveen, The Netherlands, has shown that the unique features of this new Begonia are stable and reproduced true to type in successive generations.

The cultivar Solenia Light Pink has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Solenia Light Pink'. These characteristics in combination distinguish 'Solenia Light Pink' as a new and distinct cultivar:

1. Numerous large and attractive medium pink fully double flowers that are about 7 cm in diameter.
2. Uniform and compact plant habit.
3. Dark foliage color.
4. Resistance to Powdery Mildew under commercial greenhouse conditions.
5. Outstanding weather-tolerance and garden performance.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical flowering plant of 'Solenia Light Pink'. Flower and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Aslsmeer, The Netherlands, that were flowered during the winter under commercial practice in a glass-covered greenhouse. Average day temperatures were 20° C. and average night temperatures were 18° C. Assimilation lights provided a maximum light level of 18,000 lux. Measurements and numerical values represent averages for typical flowering plants.

Botanical classification: Begonia Elatior Hybrid cultivar Solenia Light Pink.

Commercial classification: Elatior Begonia. p0 Parentage: Naturally-occurring mutation of Begonia Elation Hybrid cultivar Solenia Rosa, disclosed in U.S. Plant patent application Ser. No. 08/854,291.

Propagation:

*Type.*—Top or terminal cuttings.

*Time to rooting.*—About 14 days with soil temperatures of 23° C.

*Rooting habit.*—Fine, fibrous and well-branched.

Plant description:

*Plant form.*—Upright and rounded potted plant, uniform, compact, freely branching with good stem and stem base strength. Flowers are fully double and abundant. Plants flower continuously.

*Growth habit.*—Moderate growth rate and moderately vigorous. Appropriate for 13-cm containers. Under optimal environmental and cultural conditions, usually 10 weeks are required to produce proportional 13-cm potted plants from terminal cuttings. Vegetative shoots are formed at basal nodes and flowering shoots are formed at upper nodes.

*Plant height.*—About 25 cm.

*Leaves.*—Arrangement: Simple, alternate. Length: About 16 cm. Width: About 13 cm. Shape: Asymmetrically ovate. Apex: Acute. Base: Cordate, overlapping. Margin: Doubly serrate. Texture: Smooth. Color: Young foliage, upper surface: 147A with red tones. Young foliage, lower surface: 59A. Mature foliage, upper surface: 147A to brownish red. Mature foliage, lower surface: 59A. Venation, both surfaces: Light green. Durability: Very durable, weather-tolerant.

Flower description:

*Flowering habit.*—Fully double and large flowers arranged in compound cymes. Many cymes in flower simultaneously. Flowering continuous. Flowers persistent.

*Natural flowering season.*—Plants will flower year around regardless of daylength, however plants will flower earlier and more abundantly if daylength is 12 hours or less. Usually plants start flowering after 6 weeks of start of short day/long night treatments.

*Flowers.*—Shape: Oval, slightly asymmetrical. Diameter: About 7 cm. Depth: About 3 cm.

*Petals.*—Arrangement: Rosette. Shape: Rounded with undulating margin. Quantity per flower: Usually about 40 per flower. Color: When opening: 58C. Fully opened: Upper surface: 61D. Lower surface: 58D. Texture: Smooth, velvety, glabrous.

*Sepals.*—Arrangement: Two, opposite. Shape: Oval. Color: 144A to red.

*Reproductive organs.*—Stamens: None. Pistils: None.

Disease resistance: Plants of the cultivar Solenia Light Pink are resistant to Powdery Mildew under greenhouse conditions.

Seed production: Seed production has not been observed as reproductive organs are not formed.

It is claimed:

1. A new and distinct cultivar of Begonia plant named 'Solenia Light Pink', as illustrated and described.

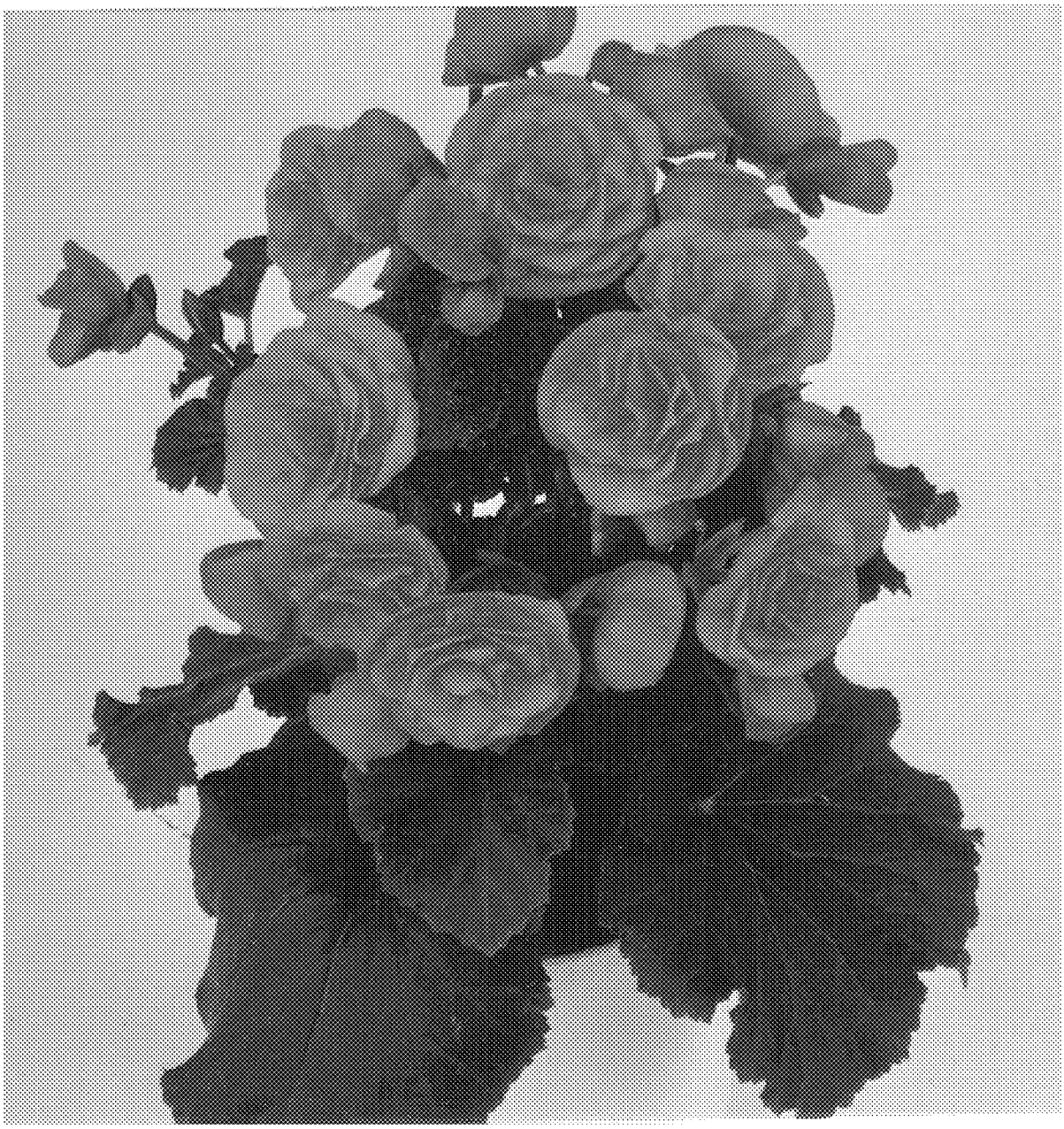

* * * * *